United States Patent [19]

Thuc

[11] Patent Number: 4,463,756
[45] Date of Patent: Aug. 7, 1984

[54] VENTILATION APPARATUS FOR ARTIFICIAL RESPIRATION

[75] Inventor: Tran N. Thuc, Omiya, Japan

[73] Assignee: Senko Medical Instrument Mfg., Co., Ltd., Japan

[21] Appl. No.: 336,629

[22] Filed: Jan. 4, 1982

[30] Foreign Application Priority Data

Jul. 3, 1981 [JP] Japan .................. 56-99180[U]
Jul. 23, 1981 [JP] Japan .................. 56-109462[U]

[51] Int. Cl.³ .................................. A61M 16/00
[52] U.S. Cl. .................. 128/204.21; 128/204.24
[58] Field of Search ............. 128/204.21, 204.24, 128/204.25, 205, 24; 137/624.14

[56] References Cited

U.S. PATENT DOCUMENTS

| | | | |
|---|---|---|---|
| Re. 29,778 | 9/1978 | Stewart | 128/204.24 |
| 3,326,237 | 6/1967 | Frick | 137/624.14 |
| 3,831,595 | 8/1974 | Valerta et al. | 128/204.24 |
| 3,872,876 | 3/1975 | Bachman | 137/624.14 |
| 3,910,303 | 10/1975 | Rydberg | 137/624.14 |
| 4,057,059 | 11/1977 | Reid, Jr. et al. | 128/204.24 |
| 4,064,895 | 12/1977 | Petersen et al. | 137/624.14 |
| 4,069,818 | 1/1978 | Schreider | 128/204.24 |
| 4,096,875 | 6/1978 | Jones et al. | 137/624.14 |
| 4,098,272 | 7/1978 | Stewart | 128/204.24 |
| 4,127,123 | 11/1978 | Bird | 128/204.25 |
| 4,215,681 | 8/1980 | Zalkin et al. | 128/204.21 |
| 4,265,237 | 5/1981 | Schwanbom et al. | 128/204.25 |
| 4,270,530 | 6/1981 | Baum | 128/204.25 |
| 4,351,329 | 9/1983 | Ellestat et al. | 128/204.21 |

Primary Examiner—William E. Kamm
Assistant Examiner—Mitchell J. Shein
Attorney, Agent, or Firm—Darby & Darby

[57] ABSTRACT

A ventilation apparatus for artificial respiration comprises a high frequency oscillation ventilator and an intermittent positive pressure ventilator, each of these ventilators being composed of a pneumatic circuit. The high frequency oscillation ventilator is connected to a respiratory gas source for feeding a respiratory gas to a patient circuit at a preselected high frequency. Also, the intermittent positive pressure ventilator is connected to the respiratory gas source for feeding the respiratory gas to the patient circuit at a preselected frequency. A shut-off valve means is provided for selectively communicating the gas source with the two ventilators whereby these ventilators are operated either alone or in combination.

12 Claims, 5 Drawing Figures

VENTILATION APPARATUS FOR ARTIFICIAL RESPIRATION

BACKGROUND OF THE INVENTION

Field of the Invention

This invention relates to a ventilation apparatus for artificial respiration which is adapted to supply respiratory gas to a patient suffering from respiratory embarrassment to effect artificial respiration.

As is well known, respiration or breathing is gas exchange by which oxygen is supplied to a living body (patient) while carbon dioxide is expelled from the living body. The lungs which function as organs of respiration consist essentially of an inverted tree of intricately branched bronchioles that communicate with thin-walled terminal alveoli swathed in a network of delicate capillaries. The gas exchange of respiration takes place between the capillaries and the alveoli into which the air is inspired. The gases subjected to the gas exchange are expelled to the atmosphere by the diffusion of the gases in the fine brochioles into which the trachea is ramified more than eighteen times, and the gas expelling is also effected through the ventilation achieved by the alternate deflation and inflation of the lungs in the relatively large bronchioles into which the trachea is ramified not more than eighteen times.

Patients suffering from respiratory embarrassment need to be subjected to artificial respiration. Various artificial respiration methods have been known in the art. These respiration methods may be broadly divided into two classes. A respiration method of one class is to assist in the above ventilation effected by the alternate deflation and inflation of the lungs. This method has long been used and is to intermittently maintain all the bronchioles and bronchi at a positive pressure so as to assist in the deflation and inflation of the lungs, thereby causing a patient to inspire and expire a respiratory gas. A typical example is an intermittent positive pressure ventilation (IPPV) method. Intermittent positive pressure ventilators for performing this method have been proposed and used extensively.

A respiration method of the other class is to apply oscillations at a frequency of 200 to 1500 cycles per minute to the lungs so that the partial pressures of $O_2$ and $CO_2$ in the blood are kept to a proper level even during apnea. This method has been proposed recently and is referred to as a high frequency oscillation (HFO) ventilation method in the trade. High frequency oscillation ventilators for performing this method have already be proposed and used.

As is well known, natural respiration or breathing is effected by inflating the lungs to maintain the bronchioles and bronchi at a negative pressure to inspire air and deflating the lungs to maintain the bronchioles and bronchi at a positive pressure to expire air. A patient suffering from respiratory embarrassment can not totally or adequately inflate and deflate the lungs for respiration. The respiratory embarrassment may be divided to various stages and broadly to two stages, i.e., (a) the stage in which the patient is completely under apnea and (b) the stage in which the patient can breathe by himself though inadequately.

The intermittent positive pressure ventilator has been quite frequently used to save patients at the above stage (a) of respiratory embarrassment. However, with the intermittent positive pressure ventilator, the lungs are intermittently maintained at a positive pressure to inspire a respiratory gas into the bronchioles, bronchi and alveoli in contrast with the natural respiration. As a result, the intermittent positive pressure ventilator has suffered from the following disadvantages:

(i) The intermittent positive pressure ventilator can only be used effectively for a patient at the above stage (a) of respiratory embarrassment and is very difficult to be used for a patient at the above stage (b) of respiratory embarrassment particularly where the patient is a baby or a child. The reason for this is that it is difficult to supply the respiratory gas through the ventilator to the respiratory tract of the patient accurately in synchronism with the inspiration of the patient. As a result, there are often occasions when the respiratory gas is supplied to the lungs of the patient during the expiration of the patient. This makes it more difficult for the patient to respire. In addition, this offers resistance to the respiratory action of the patient to cause pain to the patient.

(ii) Another disadvantage of the intermittent positive pressure ventilator is that it tends to compress the blood vessels in the thorax of the patient and disturb the blood flow so that the patient is subjected to pressure damage such as pneumothorax and suffers from the decreased heart rate. Thus, an undue load is applied to the lungs and heart of the patient. This is quite dangerous particulary when the intermittent positive pressure ventilator is applied to the patient under a serious condition who is suffering from respiratory embarrassment. The reason for the above undesirable phenomena is as follows: The ventilator of this type is designed to forcibly inspire respiratory gas intermittently into the respiratory tract of the patient so that the respiratory tract is maintained intermittently at a positive pressure. So long as the thorax of the patient is not deflated and inflated by his own respiratory action, the thorax always tends to contract. Therefore, while the respiratory tract (particulary the alveoli) is maintained at a positive pressure, the blood vessels adjacent to the alveoli are sandwiched between the alveoli and the outer portion of the thorax and are subjected to undue pressure.

In order to overcome the above disadvantage (i), there has been proposed an intermittent positive pressure ventilator of the jet type (known as a jet ventilator) in which a jet of respiratory gas is sent to the respiratory tract of the patient through a fine tube having a diameter of about 1 mm so that the supply of respiratory gas may be effected in synchronism with the natural respiration of the patient. Actually, however, this synchronism could not satisfactorily be achieved.

The high frequency oscillation ventilator mentioned above is designed to apply oscillations at a frequency of 100 to 5000 cycles per minute to the lungs. This ventilator causes the patient to respire without the inflation and deflation of his thorax. Therefore, in contrast with the intermittent positive pressure ventilator, the high frequency oscillation ventilator can supply respiratory gas to the patient without unduly maintaining the lungs at a positive pressure. Therefore, the high frequency oscillation ventilator can be used for patients both at the above stages (a) and (b) of respiratory embarrassment, and does not suffer from the above disadvantages of the intermittent positive pressure ventilator. Thus, the high frequency oscillation ventilator has such excellent advantages, but can not always be applied effectively in all situations. For example, when the high frequency oscillation ventilator is used for a patient at the above stage (a) of respiratory embarrassment, this ventilator can not achieve satisfactory results. In order to overcome this difficulty, it is necessary to apply respiratory gas to the respiratory tract to a certain degree. Therefore, the respiratory tract need to be subjected to a gas pressure (positive pressure) either continuously or intermittently to such a degree that this gas pressure is not a burden to the patient.

There have been proposed various types of high frequency oscillation ventilators and intermittent positive pressure ventilators which include those using a piston and those using a pneumatic circuit. However, such conventional ventilators are so constructed that the ventilation rate is not variable. As a result, such conventional ventilators have failed to provide a proper respiratory treatment depending upon the condition of respiratory embarrassment. Further, the conventional high frequency oscillation ventilators use a flow control valve (throttle valve) or the like for controlling the flow rate of a signal gas so as to control the supply of respiratory gas to the patient at a predetermined interval. However, the leading and trailing edges of the waveform of the signal become non-linear so that the control of the pulse width is not carried out properly. As a result, the supply and interruption of the respiratory gas to the patient can not be achieved at a regular interval.

SUMMARY OF THE INVENTION

It is therefore an object of this invention to provide a ventilation apparatus for artificial respiration which can provide a proper respiratory treatment according to the condition of a patient.

Another object is to provide an improved high frequency oscillation ventilator which can supply respiratory gas to the patient accurately at a regular interval.

According to the present invention, there is provided a ventilation apparatus for artificial respiration which comprises a gas source for supplying respiratory gas under pressure; a patient circuit for supplying the respiratory gas to a patient; a high frequency oscillation ventilator composed of a pneumatic circuit, said high frequency oscillation ventilator being connected to said gas source via a feed tube and also to said patient circuit via a feed tube so that said high frequency oscillation ventilator feeds the respiratory gas to said patient circuit at a preselected high frequency; an intermittent positive pressure ventilator composed of a pneumatic circuit, said intermittent positive pressure ventilator being connected to said gas source via a feed tube and also to said patient circuit so that said intermittent positive pressure ventilator intermittently feed the respiratory gas to said patient circuit at a preselected frequency; shut-off valve means for selectively communicating said gas source with said high frequency oscillation ventilator and said intermittent positive pressure ventilator whereby said two-ventilators are operated either alone or in combination.

Other advantages, features and additional objects of the present invention will become manifest to those versed in the art upon making reference to the detailed description and the accompanying sheets of drawings in which preferred embodiments incorporating the principles of the present invention are shown by way of illustrative examples and in which like reference characters denote corresponding parts in several view.

DESCRIPTION OF THE PREFERRED EMBODIMENTS OF THE INVENTION

Figure 1:
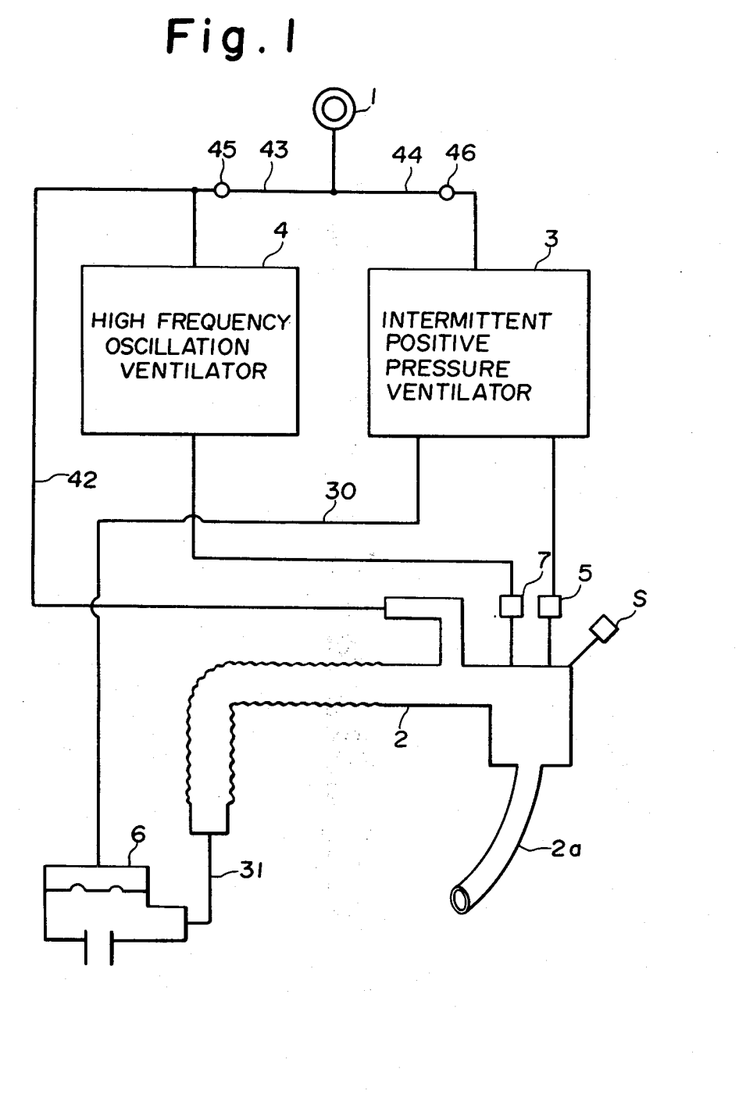
FIG. 1 is a circuit diagram of a ventilation apparatus provided in accordance with the present invention.

FIG. 1 shows a circuit diagram of a ventilation apparatus embodying this invention. The ventilation apparatus comprises a gas source 1 for supplying respiratory gas under a predetermined pressure, a patient circuit 2 to which the respiratory gas is supplied from the gas source 1, an intermittent positive pressure ventilator 3 for receiving the respiratory gas from the gas source 1 and intermittently feeding the respiratory gas to the patient circuit 2, and a high frequency oscillation ventilator 4 for receiving the respiratory gas from the gas source 1 and feeding the respiratory gas to the patient circuit 2 at a high frequency (ventilation frequency). Generally, as the respiratory gas, a mixture gas of oxygen and air is used, and a mixture gas of oxygen and nitrous oxide is used when anesthesia is required. The patient circuit 2 comprises a device for feeding the respiratory gas to the trachea of the patient, the device having an inspiration tube 2a which is adapted to be inserted through the mouth into the trachea of the patient.

The intermittent positive pressure ventilator 3 is composed of a pneumatic circuit comprising fluidic devices connected through tubes, the fluidic devices operating to change the flow lines of the circuit in response to variations in the pressure of the gas passing through the circuit. With this ventilator 3, the ventilation can be carried out at a frequency of 1 to 100 cycles per minute, and the volume of ventilation can be varried. The intermittent positive pressure ventilator 3 delivers the respiratory gas, supplied thereto from the gas source 1, to the patient circuit 2 through a feed tube 5. This ventilator 3 also delivers a signal gas from a signal gas source, contained therein, to an expiration diaphragm valve 6 through a feed tube 30.

The high frequency oscillation ventilator 4 is also composed of a pneumatic circuit. With this ventilator 4, the ventilation can be carried out at a high frequency of 100 to 5000 cycles per minute, and the volume of ventilation can be carried out. The ventilator 4 delivers the respiratory gas, supplied thereto from the gas source 1, to the patient circuit 2 through a feed tube 7.

The expiration diaphragm valve 6 is operated by the pressure of the signal gas from the intermittent positive pressure ventilator 3, and is connected to the expiration side of the patient circuit 2 through an expiration tube 31. Nagative pressure is applied to the patient circuit to promote the expiration of the gas from the lungs when the supply of the respiratory gas to the patient circuit 2 is intermittently interrupted. A supply tube S is connected to the patient circuit 2 for supplying moisture to the respiratory tract to prevent the same from being dried by the respiratory gas supplied.

Figure 2:
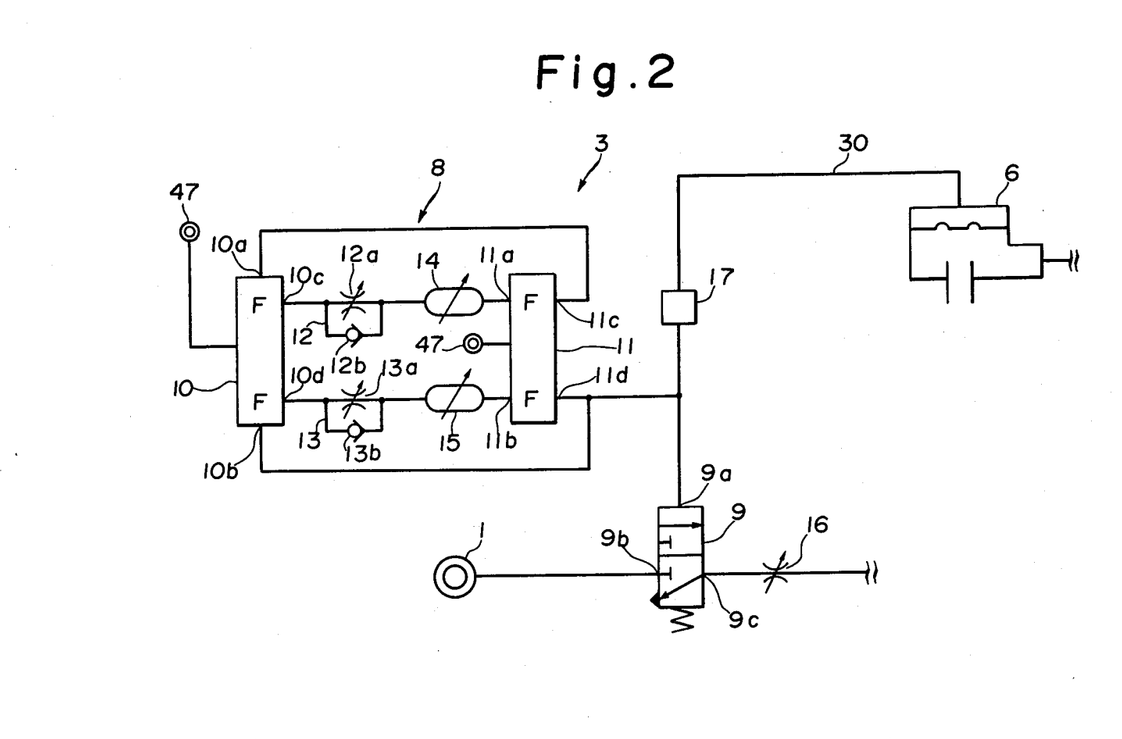
FIG. 2 is a circuit diagram of an intermittent positive pressure ventilator used in the ventilation apparatus.

The intermittent positive pressure ventilator 3 will now be described in more detail with reference to FIG. 2. The pneumatic circuit of the ventilator 3 comprises an oscillation circuit 8 and an YES device 9. The respiratory gas is supplied from the gas source 1 to a second input 9b of the YES device 9 which normally shuts off the flow of the respiratory gas. The YES device 9 passes the respiratory gas therethrough when the signal gas under a predetermined pressure is intermittently applied from the oscillation circuit 8 to a first input 9a the YES device 9. The respiratory gas passed through the YES device 9 is delivered at its output 9c to the patient circuit 2 through the feed tube 5. When the supply of the signal gas to the YES device 9 from the oscillation circuit 8 is stopped, the YES device 9 shuts off the flow of the respiratory gas.

The oscillation circuit 8 comprises a pair of flip-flop devices 10, 11, a pair of flow control devices 12, 13 and a pair of capacity-variable gas receivers 14, 15. The flow control devices 12, 13 comprises flow control valves 12a, 13a and check valves 12b, 13b, respectively. The gas receivers 14, 15 are capable of varying their capacity. The flow control device 12 and the gas receiver 14 are connected between a first output 10c of the flip-flop device 10 and a first input 11a of the flip-flop device 11. Similarly, the flow control device 13 and the gas receiver 15 are connected between a second output 10d of the flip-flop device 10 and a second input 11b of the flip-flop device 11. A first output 11c of the flip-flop 11 is connected to a first input 10a of the flip-flop device 10 while a second output 11d is connected both to the input 9a of the YES device and a second input 10b of the flip-flop device 10. The two signal gas sources 47, 47 are connected to the flip-flop devices 10, 11, respectively, for supplying the signal gas under the predetermined pressure thereto.

The interval during which the signal gas is supplied from the oscillation circuit 8 to the YES device 9 is determined by the capacity of the gas receiver 15 and the flow rate of the flow control device 13. Also, the interval during which the supply of the signal gas from the oscillation circuit 8 to the YES device 9 is stopped is determined by the capacity of the receiver 14 and the flow rate of the flow control device 12. Thus, the signal gas under the predetermined pressure is intermittently delivered from the oscillation circuit 8 both to the YES device 9 and the diaphragm valve 6.

A flow control valve 16 is provided on the feed tube 5 between the YES device 9 and the patient circuit 2 for controlling the flow rate of the respiratory gas passing therethrough. A pressure control device 17 is provided on the feed tube 30 between the oscillation circuit 8 and the diaphragm valve 6 for feeding a proper amount of the signal gas to the diaphragm valve 6. The signal gas is used only for sending the signals to the YES device 9 and the diaphragm valve 6 and is not supplied to the patient. Therefore, any suitable gas can be used as the signal gas so long as it is not of a dangerous nature.

Conventionally, gas receivers under consideration are of the type incapable of varying their capacity. When the supply (pulse width) and interruption of pulses of the signal are to be controlled only by the flow control devices 12, 13, the leading and trailing edges of the waveform of the signal become non-linear. On the other hand, when the pulse width of the signal is controlled by the use of the capacity-variable gas receivers 14, 15, the leading and trailing edges of the waveform of the signal becomes substantially linear so that the control of the pulse width is easily effected.

Figure 3:
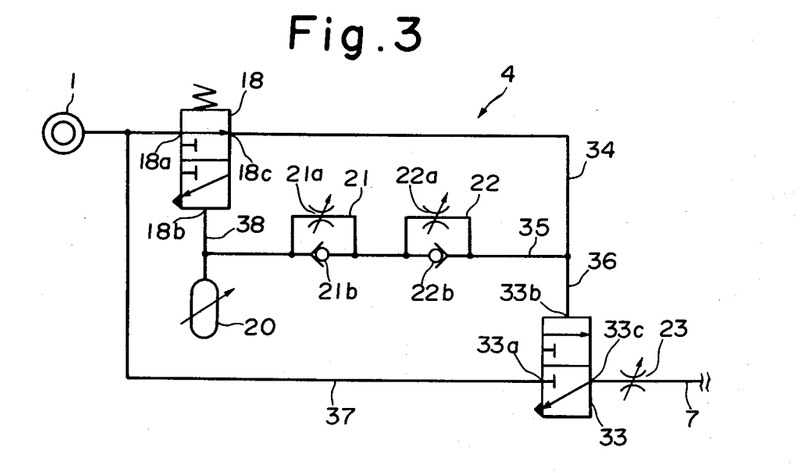
FIG. 3 is a circuit diagram of a high frequency oscillation ventilator used in the ventilation apparatus.

The high frequency oscillation ventilator 4 will now be described in more detail with reference to FIG. 3.

The pneumatic circuit of the high frequency oscillation ventilator 4 comprises a NOT device 18, a YES device 33, a capacity-variable gas receiver 20, and a pair of flow control devices 21, 22. The connection between these devices is made through gas feed tubes. The flow control devices 21, 22 comprises flow control valves 21a, 22a and check valves 21b, 22b, respectively. The gas receiver 20 and the pair of flow control valves 21, 22 are serially connected between a second input 18b of the NOT device 18 and a second input 33b of the YES device 33. The direction of flow of the check valve 21b is opposite to that of the check valve 22b. The respiratory gas is supplied from the gas source 1 directly to a first input 18a of the NOT device 18 and the first input 33a of YES device. The respiratory gas passed through the NOT device 18 is delivered at its output 18c to the flow control device 22 and also to the YES device 33 to serve as a signal gas. A flow control device 23 is provided on the feed tube 7 for controlling the flow rate of the respiratory gas fed to the patient circuit 2.

As described above, the respiratory gas is supplied from the gas source 1 to the NOT device 18 and the YES device 33. The respiratory gas passed through the NOT device 18 is delivered through a feed tube 34 and further fed through a feed tube 35 so that the respiratory gas passes through the flow control device 22 and further through the flow control device 21 at a less flow rate because of the direction of flow of the check valve 21b. The respiratory gas thus delivered is stored in the capacity-variable gas receiver 20. The respiratory gas passed through the feed tube 34 is also delivered to the YES device 33 through a feed tube 36 to act as a signal gas. When this signal gas is supplied to the second input 33b of the YES device 33, the respiratory gas, fed from the gas source 1 to the first input 33a of the YES device 33 through a feed tube 37, passes through the YES device 33 and is fed at its output 33c through the flow control valve 23 and the feed tube 7 to the patient circuit 2. Upon the lapse of a predetermined time determined by the capacity of the capacity-variable gas receiver 20 and the flow rate of the flow control device 21, the gas receiver 20 is full of the respiratory gas. Therefore, the respiratory gas passed through the flow control devices 22 and 21 is no longer introduced into the gas receiver 20 and in turn is positively fed to the second input 18b of the NOT device 18 as a signal gas. Thus, the pressure of the respiratory gas fed to the NOT device 18 through a feed tube 38 is increased so that the NOT device 18 interrupts the passage of the respiratory gas fed directly thereto from the gas source 1 and also allows the respiratory gas, passed through the feed tube 38, to pass therethrough to the ambient atmosphere. At this time, the supply of the respiratory gas to the second input 33b of the YES device 33 through the feed tubes 34 and 36 is interrupted, and the pressure of this signal gas is reduced so that the YES device 33 interrupts the passage of the respiratory gas fed through the feed tube 37. This condition is maintained until the capacity-variable gas receiver 20 exhausts the respiratory gas contained therein. This cylce of operation is repeated to supply the respiratory gas from the gas source 1 to the patient circuit 2 at a predetermined frequency. The pulse width of the signal which determines the ventilation frequency of the high frequency oscillation ventilator 4 can be easily adjusted by varying the capacity of the capacity-variable gas receiver 20, as is the case with the intermittent positive pressure ventilator 3.

It will be appreciated that the capacity-variable gas receiver 20 and the pair of flow control devices 21, 22 constitute a timer circuit. As described above, this timer circuit serves to set a time interval at which the respiratory gas is supplied to the patient circuit 2.

Figure 4:
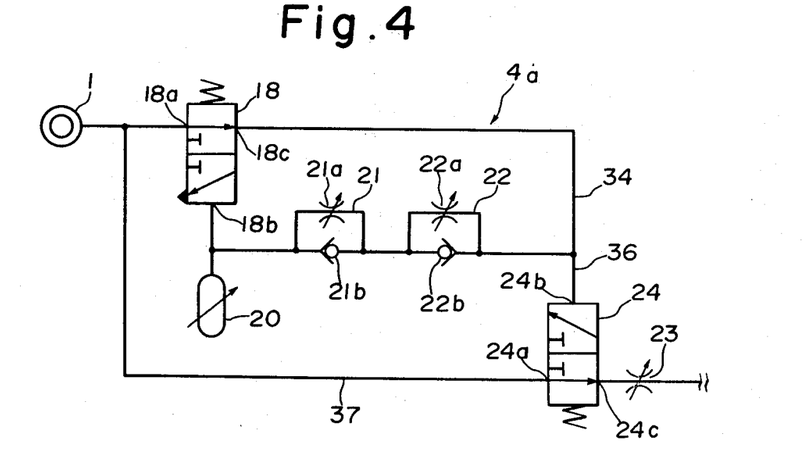
FIGS. 4 and 5 are circuit diagrams of modified high frequency oscillation ventilators, respectively.

FIG. 4 shows a pneumatic circuit of a modified high frequency oscillation ventilator 4a. This ventilator 4a differs from the high frequency oscillation ventilator 4 of FIG. 3 only in that a NOT device 24 is used instead of the YES device 33.

When the respiratory gas is fed as a signal gas through the NOT device 18 and feed tubes 34 and 36 to a second input 24b of the NOT device 24, the NOT device 24 interrupts the passage of the respiratory gas fed through the feed tube 37 to its first input 24a so that the supply of the respiratory gas to the patient circuit 2 at its output 24c is interrupted. In contrast, when the signal gas is not delivered to the second input 24b of the NOT device 24 through the feed tubes 34 and 36, the NOT device 24 passes the respiratory gas, fed through the feed tube 37, to the patient circuit 2. Thus, with this ventilation 4a, the supply and interruption of the respiratory gas to the patient circuit 2 is carried out in a manner reverse to that in the high frequency oscillation 4 of FIG. 3, but it will be appreciated that these two ventilators 4 and 4a perform the same function.

Figure 5:
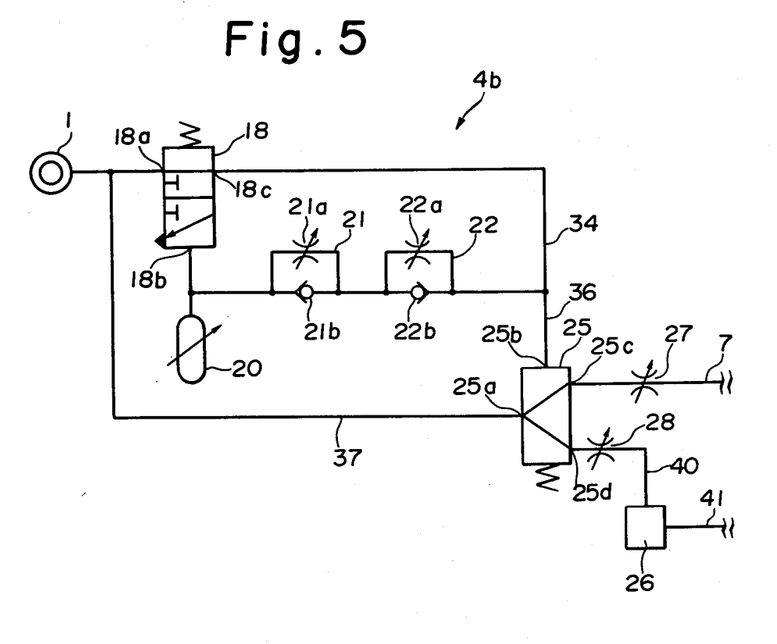

FIG. 5 shows a pneumatic circuit of another modified high frequency oscillation ventilator 4b. This ventilator 4b differs from the high frequency oscillation ventilator 4 of FIG. 3 in that a flow switching device 25 and a negative pressure generator 26 are provided instead of the YES device 33. When the respiratory gas is fed as a signal gas through the NOT device 18 and the feed tubes 34, 36 to a second input 25b of the flow switching device 25, the flow switching device 25 switches its passageway in such a manner that the respiratory gas fed through the feed tube 37 to its first input 25a is passed through the flow switching device 25 at its second output 25d to the negative pressure generator 26 via a feed tube 40. On the other hand, when the NOT device 18 interrupts the passage of the signal gas, the flow switching device 25 switches its passageway in such a manner that the respiratory gas fed through the feed tube 37 is delivered therethrough at its first output 25c to the patient circuit 2 via the feed tube 7. The negative pressure generator 26 receives the respiratory gas from the flow switching device 25 to generate negative pressure (suction). The negative pressure generator 26 is connected via a tube 41 to the expiration side of the patient circuit 2 for promoting the expiration of the patient. Flow control valves 27 and 28 are provided on the feed tubes 7 and 40, respectively. With this ventilator 4b, the inspiration and expiration of the respiratory gas are quite positively carried out periodically depending on the pulse width determined by the timer circuit composed of the capacity-variable gas receiver 20 and the flow control devices 21, 22. Therefore, a more effective ventilation is carried out.

As shown in FIG. 1, the gas source 1 is connected directly to the patient circuit 2 via feed tubes 42 and 43 for supplying the respiratory gas thereto to maintain the concentration of oxygen in the respiratory gas in the lungs at a higher level.

The operation of the ventilation apparatus will now be described with reference to FIG. 1.

First, when only the intermittent positive pressure ventilator 3 is to be used according to the condition of the patient, the feed tube 43 is shut off by a shut-off valve 45 provided thereon to interrupt the supply of the respiratory gas to the high frequency oscillation ventilator 4 and the supply of the respiratory gas to the patient circuit 2 via the feed tube 42. Thus, the respiratory gas is supplied from the gas source 1 only to the intermittent positive pressure ventilator 3. The ventilator 3 can perform the ventilation at a preselected frequency of 1 to 100 cycles per minute so that the respiratory gas is periodically supplied to the patient circuit 2 via the feed tube 5. At the same time, the diaphragm valve 6 is activated to positively exhaust the used gas periodically from the lungs of the patient through the patient circuit 2 to the ambient atmosphere.

Next, when only the high frequency oscillation ventilator 4 is to be used according to the condition of the patient, a feed tube 44 is shut off by a shut-off valve 46 provided thereon to interrupt the supply of the respiratory gas to the intermittent positive pressure ventilator 3. The connection between the patient circuit 2 and the diaphragm valve 6 through the expiration tube 31 is released, and the expiration side of the patient circuit 2 is caused to be in communication with the ambient atmosphere. The ventilator 4 can perform the ventilation at a preselected frequency of 100 to 5000 cycles per minute so that the respiratory gas is periodically supplied to the patient circuit 2 via the feed tube 7. The respiratory gas is supplied from the gas source 1 directly to the patient circuit 2 through the feed tubes 43 and 42 to maintain the concentration of oxygen in the respiratory gas in the lungs at a higher level, as described above. When the high frequency oscillation ventilator 4b of FIG. 5 is to be used, the negative pressure generator 26 is connected to the expiration side of the patient circuit 2 through the tube 41.

Finally, when both the intermittent positive pressure ventilator 3 and the high frequency oscillation ventilator 4 are to be used to treat a patient under a serious condition, the respiratory gas is supplied from the gas source 1 to the two ventilators 3 and 4. The respiratory gas is also supplied from the gas source 1 directly to the patient circuit 2 through the feed tubes 43 and 42. With this method, the ventilation is effected in the most effective manner.

As described above, with the ventilation apparatus of this invention, the intermittent positive pressure ventilator and the high frequency oscillation ventilator can be used either alone or in combination, depending on the condition of the patient. Further, by virtue of the provision of the capacity-variable gas receivers, the respiratory gas can be supplied to the patient at a regular interval since the leading and trailing edges of the waveform of the signal becomes substantially linear, which facilitates the control of the pulse width.

While the ventilation apparatus according to the invention has been specifically shown and described herein, the invention itself is not to be restricted by the exact showing of the drawings or the description thereof.

What is claimed is:

1. A ventilation apparatus for artificial respiration which comprises:
   (a) a gas source for supplying respiratory gas under pressure;
   (b) a patient circuit for supplying the respiratory gas to a patient;
   (c) a high frequency oscillation ventilator composed of a pneumatic circuit, said high frequency oscillation ventilator being connected to said gas source via a feed tube and also to said patient circuit via a feed tube so that said high frequency oscillation ventilator feeds the respiratory gas to said patient circuit at a preselected high frequency;

(d) an intermittent positive pressure ventilator composed of a pneumatic circuit, said intermittent positive pressure ventilator being connected to said gas source via a feed tube and also to said patient circuit so that said intermittent positive pressure ventilator intermittently feed the respiratory gas to said patient circuit at a preselected frequency; and (e) shut-off valve means for selectively communicating said gas source with said high frequency oscillation ventilator and said intermittent positive pressure ventilator for operating said two ventilators either alone or in combination.

2. A ventilation apparatus according to claim 1, in which said gas source is also connected to said patient circuit for supplying the respiratory gas thereto.

3. A ventilation apparatus for artificial respiration which comprises:

(a) a gas source for supplying respiratory gas under pressure;

(b) a patient circuit for supplying the respiratory gas to a patient;

(c) a high frequency oscillation ventilator composed of a pneumatic circuit, said high frequency oscillation ventilator being connected to said gas source via a feed tube and also to said patient circuit via a feed tube so that said high frequency oscillation ventilator feeds the respiratory gas to said patient circuit at a preselected high frequency;

(d) an intermittent positive pressure ventilator composed of a pneumatic circuit, said intermittent positive pressure ventilator being connected to said gas source via a feed tube and also to said patient circuit so that said intermittent positive pressure ventilator intermittently feed the respiratory gas to said patient circuit at a preselected frequency; and (e) shut-off valve means for selectively communicating said gas source with said high frequency oscillation ventilator and said intermittent positive pressure ventilator for operating said two ventilators either alone or in combination, wherein the pneumatic circuit of said intermittent positive pressure ventilation comprises a signal gas source for supplying a signal gas, a YES device having first and second inputs and one output, and an oscillation circuit connected to said signal gas source, said oscillation circuit being connected to the first input of said YES device for intermittently sendng the signal gas thereto, said gas source of the respiratory gas being connected to the second input of said YES device, and the output of said YES device being connected to said patient circuit, whereby said YES device delivers the respiratory gas to said patient circuit when the signal gas is fed from said oscillation circuit to the first input of said YES device.

4. A ventilation apparatus according to claim 3, in which said intermittent positive pressure ventilator further comprises an expiration diaphragm valve connected to said oscillation circuit for receiving the signal gas therefrom, said diaphragm valve being also connected to an expiratory side of said patient circuit, whereby a negative pressure is applied to said patient circuit when the supply of the respiratory gas to the patient circuit is intermittently interrupted.

5. A ventilation apparatus according to claim 3, in which said oscillation circuit comprises first and second flip-flop devices, first and second flow control devices and first and second capacity-variable gas receivers, the flow control device and the first gas receiver being connected between a first output of the first flip-flop device and a first input of the second flip-flop device, the second flow control device and the second gas receiver being connected between a second output of the first flip-flop device and a second input of the second flip-flop, a first output of the second flip-flop device being connected to a first input of the first flip-flop device while a second output is connected both to the first input of said YES device and a second input of the first flip-flop device, and said signal gas source being connected to the first and second flip-flop devices.

6. A ventilation apparatus according to any one of claims 3 to 5, in which the pneumatic circuit of said high frequency oscillation ventilator comprises a NOT device having first and second inputs and one output, a YES device having first and second inputs and one output, a pair of flow control devices, and a capacity-variable gas receiver, said gas source of the respiratory gas being connected to the first input of said NOT device and the first input of said YES device, the output of said NOT device being connected to the second input of said YES device through a gas feed tube, and said capacity-variable gas receiver and said pair of flow control devices being serially connected between the second input of said NOT device and said gas feed tube, whereby said YES device passes the respiratory gas, supplied to its first input, to said patient circuit when the respiratory gas is supplied through said NOT device to the second input of said YES device, and whereby when the respiratory gas, passed through said NOT device and said pair of flow control devices fills in said capacity-variable gas receiver, the respiratory gas is delivered to the second input of said NOT device whereupon said NOT device interrupts the passage of the respiratory gas supplied to its first input.

7. A ventilation apparatus according to any one of claims 3 to 5, in which the pneumatic circuit of said high frequency oscillation ventilator comprises a first NOT device having first and second inputs and one output, a second NOT device having first and second inputs and one output, a pair of flow control devices and a capacity-variable gas receiver, said gas source of the respiratory gas being connected to the first input of said first NOT device and the first input of said second NOT device, the output of said first NOT device being connected to the second input of said second NOT device through a gas feed tube, and said capacity-variable gas receiver and said pair of flow control devices being serially connected between the second input of said first NOT device and said gas feed tube, whereby said second NOT device passes the respiratory gas, supplied to its first input, to said patient circuit when the respiratory gas is not supplied through said first NOT device to the second input of said second NOT device, and whereby when the respiratory gas, passed through said first NOT device and said pair of flow control devices, fills in said capacity-variable gas receiver, the respiratory gas is delivered to the second output of said first NOT device whereupon said first NOT device interrupts the passage of the respiratory gas supplied to its first input.

8. A ventilation apparatus according to either one of claims and 5 in which the pneumatic circuit of said high frequency oscillation ventilator comprises a NOT device having first and second inputs and one output, a flow switching device having first and second inputs and one output, a pair of flow control devices, a capacity-variable gas receiver and a negative pressure generator, said gas source of the respiratory gas being connected to the first input of said NOT device and the first input of said flow switching device, the output of said NOT device being connected to the second input of said flow switching device through a gas feed tube, and said capacity-variable gas receiver and said pair of flow control devices being serially connected between the second input of said NOT device and said gas feed tube, said negative pressure generator being connected between the second output of said flow switching device and said patient circuit, the first output of said flow switching device being connected to said patient circuit, whereby said flow switching device passes the respiratory gas, supplied to its first input, to said patient circuit when the respiratory gas is not supplied through said NOT device to the second input of said flow switching device, and whereby said flow switching device passes the respiratory gas, supplied to its first input, to said negative pressure generator when the respiratory gas is supplied through said NOT device to the second input of said flow switching device, and whereby when the respiratory gas, passed through said NOT device and said pair of flow control devices, fills in said capacity-variable gas receiver, the respiratory gas is delivered to the second input of said first NOT device whereupon said NOT device interrupts the passage of the respiratory gas supplied to its first input.

9. A ventilation apparatus for artificial respiration which comprises:
- (a) a gas source for supplying respiratory gas under pressure;
- (b) a patient circuit for supplying the respiratory gas to a patient;
- (c) a high frequency oscillation ventilator composed of a pneumatic circuit, said high frequency oscillation ventilator being connected to said gas source via a feed tube and also to said patient circuit via a feed tube so that said high frequency oscillation ventilator feeds the respiratory gas to said patient circuit at a preselected high frequency;
- (d) an intermittent positive pressure ventilator composed of a pneumatic circuit, said intermittent positive pressure ventilator being connected to said gas source via a feed tube and also to said patient circuit so that said intermittent positive pressure ventilator intermittently feed the respiratory gas to said patient circuit at a preselected frequency; and
- (e) shut-off valve means for selectively communicating said gas source with said high frequency oscillation ventilator and said intermittent positive pressure ventilator for operating said two ventilators either alone or in combination,
- (f) a first valve connected to said gas source;
- (g) a timer circuit connected to said first valve and being responsive to a preselected volume of the respiratory gas, passed through said first valve, for feeding a signal to said first valve at a preselected high frequency for switching the flow of the respiratory gas through said first valve; and
- (h) a second valve connected directly to said gas source and said first valve so that said second valve switches the flow of the respiratory gas fed directly from said gas source in responsive to the supply of the respiratory gas fed through said first valve.

10. A high frequency oscillation ventilator according to claim 9, in which the pneumatic circuit of said high frequency oscillation ventilator comprises a NOT device as said first valve which has first and second inputs and one output, a YES device as said second valve which has first and second inputs and one output, a pair of flow control devices, and a capacity-variable gas receiver, said flow control devices and said capacity-variable device constituting said timer circuit, said gas source of the respiratory gas being connected to the first input of said NOT device and the first input of said YES device, the output of said NOT device being connected to the second input of said YES device through a gas feed tube, and said capacity-variable gas receiver and said pair of flow control devices being serially connected between the second input of said NOT device and said gas feed tube, whereby said YES device passes the respiratory gas, supplied to its first input, to said patient circuit when the respiratory gas is supplied through said NOT device to the second input of said YES device, and whereby when the respiratory gas, passed through said NOT device and said pair of flow control devices fills in said capacity-variable gas receiver, the respiratory gas is delivered to the second input of said NOT device whereupon said NOT device interrupts the passage of the respiratory gas supplied to its first input.

11. A high frequency oscillation ventilator according to claim 9, in which the pneumatic circuit of said high frequency oscillation ventilator comprises a first NOT device as said first valve which has first and second inputs and one output, a second NOT device as said second valve which has first and second inputs and one output, a pair of flow control devices and a capacity-variable gas receiver, said flow control devices and said capacity-variable device constituting said timer circuit, said gas source of the respiratory gas being connected to the first input of said first NOT device and the first input of said second NOT device, the output of said first NOT device being connected to the second input of said second NOT device through a gas feed tube, and said capacity-variable gas receiver and said pair of flow control devices being serially connected between the second input of said first NOT device and said gas feed tube, whereby said second NOT device passes the respiratory gas, supplied to its first input, to said patient circuit when the respiratory gas is not supplied through said first NOT device to the second input of said second NOT device, and whereby when the respiratory gas, passed through said first NOT device and said pair of flow control devices, fills in said capacity-variable gas receiver, the respiratory gas is delivered to the second input of said first NOT device whereupon said first NOT device interrupts the passage of the respiratory gas supplied to its first input.

12. A high frequency oscillation ventilator according to claim 9, in which the pneumatic circuit of said high frequency oscillation ventilator comprises a NOT device as said first valve which has first and second inputs and one output, a flow switching device as said second valve which has first and second inputs and one output, a pair of flow control devices, a capacity-variable gas receiver and a negative pressure generator, said flow control devices and said capacity-variable device constituting said timer circuit, said gas source of the respiratory gas being connected to the first input of said NOT device and the first input of said flow switching device, the output of said NOT device being connected to the second input of said flow switching device through a gas feed tube, and said capacity-variable gas receiver and said pair of flow control devices being serially connected between the second input of said NOT device and said gas feed tube, said negative pressure generator being connected between the second output of said flow switching device and said patient circuit, the first output of said flow switching device being connected to said patient circuit, whereby said flow switching device passes the respiratory gas, supplied to its first input, to said patient circuit when the respiratory gas is not supplied through said NOT device to the second input of said flow switching device, and whereby said flow switching device passes the respiratory gas, supplied to its first input, to said negative pressure generator when the respiratory gas is supplied through said NOT device to the second input of said flow switching device, and whereby when the respiratory gas, passed through said NOT device and said pair of flow control devices, fills in said capacity-variable gas receiver, the respiratory gas is delivered to the second input of said first NOT device whereupon said NOT device interrupts the passage of the respiratory gas supplied to its first input.

* * * * *

UNITED STATES PATENT AND TRADEMARK OFFICE
CERTIFICATE OF CORRECTION

PATENT NO. : 4,463,756
DATED : August 7, 1984
INVENTOR(S) : Tran N. Thuc

It is certified that error appears in the above-identified patent and that said Letters Patent is hereby corrected as shown below:

On the title page, the name of the inventor should be changed from "Tran N. Thuc" to --Tran N. Phuc--.

Signed and Sealed this

Twenty-ninth Day of October 1985

[SEAL]

Attest:

Attesting Officer

DONALD J. QUIGG

Commissioner of Patents and Trademarks—Designate